(12) United States Patent
Albrecht et al.

(10) Patent No.: US 12,025,785 B2
(45) Date of Patent: Jul. 2, 2024

(54) MEDICAL-OPTICAL OBSERVATION APPARATUS WITH OPTO-ACOUSTIC SENSOR FUSION

(71) Applicant: Carl Zeiss Meditec AG, Jena (DE)

(72) Inventors: Christian Albrecht, Aalen (DE); Stefan Saur, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 613 days.

(21) Appl. No.: 17/217,756

(22) Filed: Mar. 30, 2021

(65) Prior Publication Data

US 2021/0302708 A1 Sep. 30, 2021

(30) Foreign Application Priority Data

Mar. 30, 2020 (DE) ...................... 10 2020 108 796.9

(51) Int. Cl.
G02B 21/00 (2006.01)
G02B 21/36 (2006.01)
G06N 20/00 (2019.01)

(52) U.S. Cl.
CPC ....... *G02B 21/0012* (2013.01); *G02B 21/361* (2013.01); *G02B 21/365* (2013.01); *G06N 20/00* (2019.01)

(58) Field of Classification Search
CPC .......................... G02B 21/0012; G02B 21/361; G02B 21/365; G06N 20/00
USPC ................................................ 359/305, 306
See application file for complete search history.

(56) References Cited

U.S. PATENT DOCUMENTS

| 2012/0179039 A1* | 7/2012 | Pelissier ............... H04N 19/61 600/443 |
| 2016/0055886 A1 | 2/2016 | Saur et al. |
| 2018/0071047 A1 | 3/2018 | Suzuki et al. |
| 2018/0242958 A1 | 8/2018 | Dayton et al. |
| 2018/0366231 A1 | 12/2018 | Wolf et al. |
| 2019/0057760 A1 | 2/2019 | Schwartz et al. |
| 2019/0125319 A1 | 5/2019 | Enoki et al. |
| 2019/0324252 A1 | 10/2019 | Mak et al. |

FOREIGN PATENT DOCUMENTS

JP 6553210 B2 * 7/2019 ............. A61B 18/20

OTHER PUBLICATIONS

Roberts D.W, et al, A frameless stereotaxic integration of computerized tomographic imaging and the operating microscope, Oct. 1986, vol. 65, New Hampshire.
Office Action issued in German Patent Application No. DE 10 2020 108 796.9 (from which this application claims priority), dated Jan. 29, 2021 and English language machine translation thereof.

* cited by examiner

*Primary Examiner* — William Choi
(74) *Attorney, Agent, or Firm* — Ewers IP Law PLLC; Falk Ewers

(57) ABSTRACT

A medical-optical observation apparatus is provided, which includes an image recording device with an optical system and an optical field of view, for recording optical signals from an operating region, and a microphone device with an acoustic directional area, for the directed recording of acoustic signals with reference to the operating region, and wherein the acoustic directional area includes the optical field of view.

20 Claims, 1 Drawing Sheet

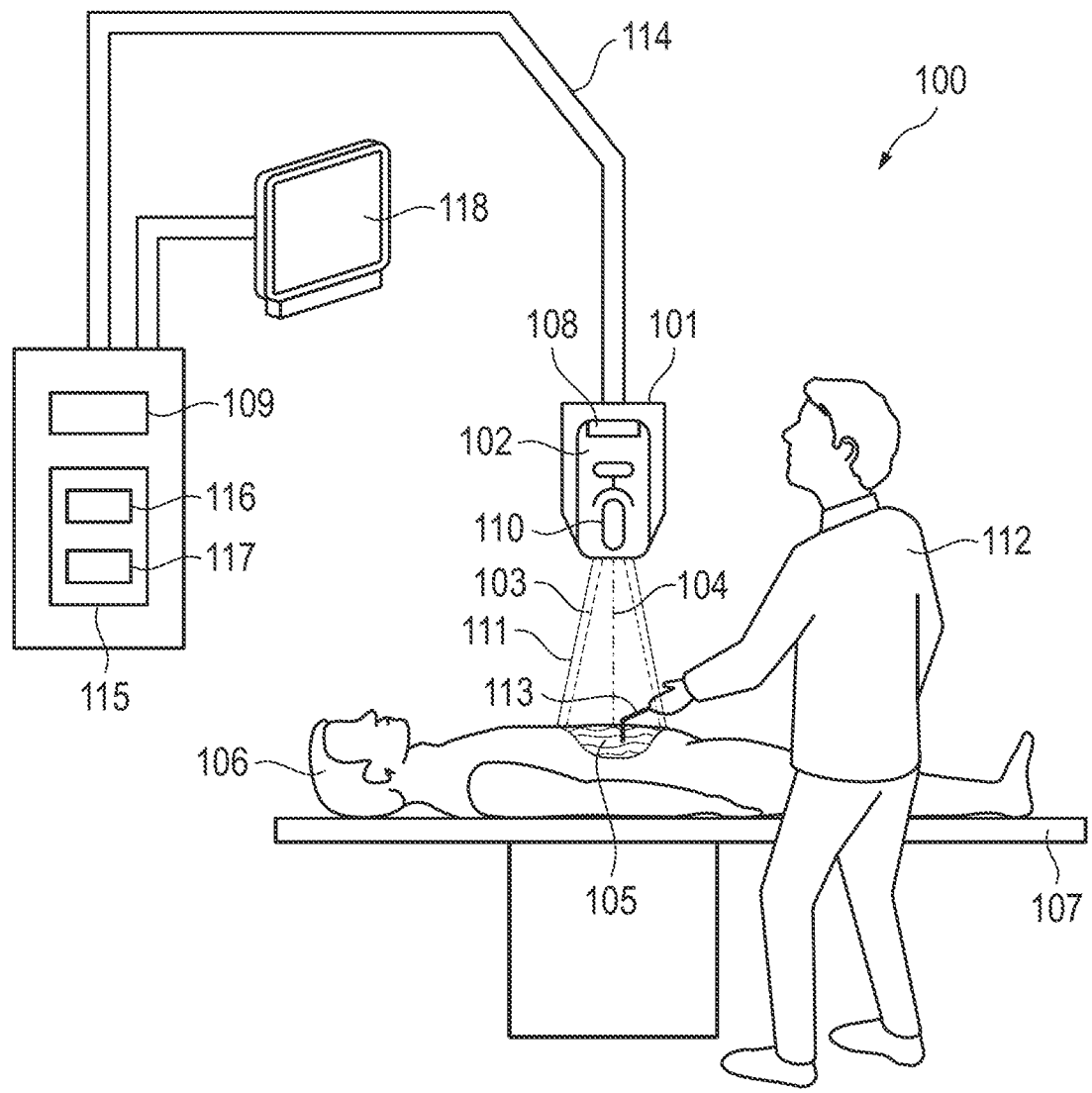

MEDICAL-OPTICAL OBSERVATION APPARATUS WITH OPTO-ACOUSTIC SENSOR FUSION

CROSS REFERENCE TO RELATED APPLICATIONS

This application claims priority to German patent application DE 10 2020 108 796.9, filed Mar. 30, 2020, the entire content of which is incorporated herein by reference.

TECHNICAL FIELD

The present disclosure relates to a medical-optical observation apparatus with opto-acoustic sensor fusion, a computer program product suitable for the operation thereof, and a non-volatile computer-readable storage medium.

BACKGROUND

A medical-optical observation apparatus includes at least one component which includes an optical system used to capture light rays from an observed area in order to generate an image in an image plane, which image can be observed or recorded, i.e., stored, wherein the observed area is a medically relevant area, e.g., during the treatment of a patient, in particular an operating region, i.e., a site, of the patient during a surgical operation. In this case, the medical-optical observation apparatus can be or include a surgical microscope, in particular.

To document a performed medical treatment procedure, in particular a surgical operation, for example for subsequent evaluation or checking, or else for training purposes, and to unburden the physician during the subsequent documentation, in particular with the creation of the surgery report, it may be expedient to record information in respect of a performed operation already during the performance thereof. In this context, it is particularly advantageous for evaluation purposes to recognize the various phases of the course of an operation. The recognition of phases of the course of an operation, i.e., operating phases, can also be used already during the operation, for example to automatically control modalities of the medical-optical observation apparatus on the basis of the current phase. When using a medical-optical observation apparatus such as a surgical microscope, this can be implemented when recording and evaluating image data over the course of time, in particular.

By way of example, in US 2019/0324252 A1, images are recorded and analyzed during an operation phase. If certain features that should be assigned to a different operation phase are detected therein, the zoom and the lighting, for example, are adapted, additional menus are superimposed or the image representation is altered.

However, it is possible that a recognition of phase based only on automated image data evaluation has only an insufficient prediction accuracy.

Therefore, there are trials where other sensor data are included, and the recognition is based on the fusion or combination of image data and other sensor signals. Thus, in the case of a surgical microscope, e.g., image data in combination with sensor data which reproduce current settings of the surgical microscope, for example the stand pose, the zoom and/or the choice of imaging mode, can still yield prediction accuracies that are too low.

By way of example, US 2016/0055886 A1 presents a method, with which the video data of a surgical operation recorded by a surgical microscope can be divided into a chapter structure by also taking account of parameter values of the surgical microscope.

However, the settings of the surgical microscope over the course of an operation are subject to only relatively few changes by the user, i.e., the surgeon, over relatively long periods of time, and so a resolution or accuracy of the phase determination of the course of the operation can only be improved a little.

In US 2019/0057760 A1, text data from the medical file of the patient are combined with video recordings and audio recordings for the purposes of the automated generation of documentation of clinical events, and hence an overall overview is generated in an automated manner. Provision is made here, inter alia, of generating speech recordings of the medical staff during the course of the treatment and of automatically with voice-recognition methods converting these recordings into text that is included in the representation.

US 2018/0366231 A1 shows that key events in videos of surgical operations can be recognized by way of a video analysis, the user then selecting the most relevant recognized key events therefrom for an overview of the course of the operation and it then also being possible to assign said key events to data from the electronically available patient file and audio recordings, in particular speech recordings, from the operating theater.

Instead of evaluating video recordings, provision can also be made for the behavior or the state of the surgical instrument to be monitored and evaluated. Thus, US 2018/0242985 A1 shows for example that sensor data of the surgical instrument can be monitored, for example temperature, rotational speed and drill noises of a surgical drill in the case shown, wherein the noises of the drill recorded by a microphone on the drill are intended to supply information about the currently drilled layer.

US 2018/0071047 A1, too, shows that a surgical instrument, rod-shaped surgical forceps in the example shown, can be connected to a vibration sensor or microphone in order to allow conclusions to be drawn about changes in the state at the distal end from signals recorded at the proximal end of the rod, wherein provision can moreover be made for the surgical instrument to be guided by the surgeon with visual assistance by a video microscope.

While a combined evaluation of sensor data of the surgical microscope with the recorded image data does not always supply sufficiently accurate results when improving the distinction between different phases of the course of an operation and although it is known that audio signals in the form of speech recordings of the surgeon or operation noises of the utilized surgical instruments can likewise supply evaluable information about the course of the operation, it has however not been shown how the accuracy of a phase recognition of the course of an operation can in fact be improved, where possible without additionally restricting the surgeon's freedom when carrying out the surgery, for example by virtue of the latter being expected to provide meaningful verbal commentary while performing the surgery or having to use surgical instruments specifically set up to record noises.

SUMMARY

It is therefore an object of the present disclosure to provide a medical-optical observation apparatus which offers the option of easily realizing great accuracy when recognizing phases of the course of an operation.

This object is achieved by a medical-optical observation apparatus with opto-acoustic sensor fusion, by a computer program product suitable for the operation thereof, and by a non-volatile computer-readable storage medium as described herein.

According to a first aspect of the disclosure, a medical-optical observation apparatus includes an image recording device with an optical system and an optical field of view, for recording optical signals from an operating region, and a microphone device with an acoustic directional area, for the directed recording of acoustic signals with reference to the operating region, wherein the acoustic directional area includes the optical field of view.

According to an aspect of the disclosure, provision is made for a storage device for storing the optical signals to be assigned to the image recording device and a storage device for storing the acoustic signals to be assigned to the microphone device, the optical and acoustic signals being able to be stored with a common time reference such that it is possible to temporally relate the signals to one another during an evaluation.

An image recording device includes an optical system, i.e., an arrangement of components generating an optical image representation, such as lenses, mirrors, prisms and stops, e.g., an objective lens of a microscope, and an optical sensor, i.e., an image sensor, and a storage device in order to record, i.e., store, the optical sensor data at least intermittently. If the optical sensor is an electronic image sensor, electronic representations of the optical signals are stored. Depending on the embodiment of the image recording device, which may be a camera, the latter can itself include the storage device or it can include an interface, with which it is connected or connectable to a suitable storage device. The optical field of view of the image recording device is the region in the angle of view of the image recording device, within which events can be captured and recorded. By way of example, it depends on the settings of the optical systems and possibly on the size of the utilized image sensor. The image recording device serves to record optical signals of the operating region, i.e., the site of the patient in the case of a surgical intervention, wherein the optical field of view includes the operating region or at least a section thereof. Optical signals, i.e., image signals, are recorded during the course of an operation, in particular continuously or at regular time intervals as a video.

A microphone device is an audio recording device with at least one acoustic sensor, i.e., at least one microphone, for capturing acoustic signals, i.e., noises, that is to say audio signals, and the recording, i.e., storage, thereof in a storage device at least on an intermittent basis. The frequency range of the acoustic sensor is at least also in the human audible range, with the human audible range comprising a frequency range between 16 Hz and 20,000 Hz. Typically, the frequency range of the acoustic sensor includes at least the entire frequency range of the human audible range. If the microphone device performs analog/digital conversion, digital electronic representations of the acoustic signals are stored.

Instead of storing directly digitized sampled values as an electronic representation of the acoustic signal, provision can also be made for encoding or compression of the audio data and/or parameterization of the signal curve to be initially undertaken for preprocessing purposes and/or for a descriptive model of the acoustic signals to be initially generated and parameterized, for example with the aid of machine learning methods, wherein then the result of the pre-processing, i.e., for example, parameter values, is stored as an electronic representation of the acoustic signal. In one exemplary embodiment, provision can also be made for different variants of the acoustic signal to be generated and stored as electronic representations, for example on the basis of different sampling rates, encoding methods or compression rates, different filtering, different descriptive models or parameterization rules. (A corresponding statement also applies to the generation and storage of electronic representations of the optical signals recorded by the image recording device.)

Depending on the embodiment of microphone device, the latter can itself include the storage device or it can include an interface, with which it is connected or connectable to a suitable storage device. Provision can be made for the electronic representations of the acoustic and the optical signals to be stored in the same storage device. In any case, provision is made for the acoustic and the optical signals, or the electronic representations thereof, to be stored with a common time reference, e.g., by way of common or synchronized timestamps, such that it is possible to temporally relate the signals to one another or evaluate the signals in synchronized fashion within the scope of an evaluation. The acoustic directional area of the microphone device denotes a region in which the sensitivity of the microphone device, i.e., the output voltage in relation to the sound pressure in the case of a microphone or electroacoustic transducer, is very high such that even very quiet acoustic signals can be captured, whereas the damping of the captured acoustic signals is very high outside of the directional area such that these do not generate a sensor signal or only generate a very weak sensor signal. The transmission of the acoustic signals through the directional area is implemented at least substantially through the air; that is to say, the source of the acoustic signal is not physically connected to the microphone device. If the microphone device only includes one microphone, the acoustic angle of incidence, under which incident audio signals are not masked or are at least strongly dampened, can define the directional area. In the case of microphone devices with a plurality of microphones, the directional area may be able to be shaped accordingly where necessary. The size of the acoustic directional area is frequency dependent.

Acoustic signals related to the operating region are acoustic signals from noise sources within the operating region itself, but also from operating instruments and other auxiliary means, e.g., clamps, as noise sources if these are used within the operating region. Further examples of noise sources which generate acoustic signals related to the operating region are, inter alia, the use of a suction device for aspirating tissue remains and liquids, wherein a pump-like noise is generated which may have a specific characteristic depending on the tissue consistency, e.g., soft, hard, etc., rinsing of the site with water, with a "blubber noise" being generated, since the water syringe used for the rinsing is usually not captured in the optical field of view, only the noise connected therewith is detectable in this case, the obliteration of tissue with bipolar forceps, with a "sizzling noise" being generated, placing a clip during an aneurysm operation, "metallic noises" arise in the process since the clip is spread and then locked, comminuting tissue with ultrasound, e.g. with a CUSA (cavitron ultrasonic surgical aspirator) or with a phaco system, from identifying the presence (not the localization) of ultrasonic signals, it is possible to deduce the use of a corresponding ultrasonic system and, from this, the presence of a specific phase of operation; the insertion of an intraocular lens is connected to an "unfolding noise, noises of ultrasonic applicators, e.g., during phacoemulsification within the scope of cataract surgery, noises of vitrectomes for removing the vitreous humor of an eye, in this case, differences in the noises may occur depending on whether tissue is currently being cut or whether the apparatus is running without load.

According to an aspect of the disclosure, provision is made for the acoustic directional area to include the optical field of view. Consequently, the acoustic directional area also includes the operating region. If the optical field of view only includes a section of the operating region, for example because the section was zoomed into, the acoustic field of view includes at least this section of the operating region such that all acoustic signals directly related to the operating region, to the extent it is located within the field of view of the image recording device, can be recorded while all other noises, i.e., noises from sound sources outside of the directional area, are masked or strongly dampened. Thus, over the course of the operation, it is possible to record many acoustic signals, some of which are also very quiet, which contain a plurality of information items about the course of the operation. By way of example, the quiet noise of a suction device when aspirating a liquid in the operating region or the short sound of the insertion of a clip, e.g., a clamp, during the operation can help with the identification or assignment of a process to a specific phase during the course of the surgical operation. In this case, the acoustic information offers complementary information to the optical image information. The acoustic information can also be of assistance when evaluating an operation report and can help with the detection of anomalies, for example if deviations are determined in relation to a stored standard course of a comparable operation.

In one exemplary embodiment, the microphone device is set up to record acoustic signals from noise sources in the optical field of view of the image recording device and dampen other acoustic signals. This offers the additional advantage that, depending on the extent of the acoustic directional area beyond the optical field of view, there is a better avoidance of undamped recording of other noises or speech.

In an exemplary embodiment, provision is made for the acoustic directional area to substantially correspond with the optical field of view. In this way, all acoustic signals recorded by the microphone device relate, as a rule, to the operating region shown in the optical field of view of the image recording device, while other sources of acoustic signals are masked or damped very strongly. Moreover, it is thus possible to be able to use other acoustic signals outside of the acoustic directional area without these, as disturbance noises, reducing the utility of the signals recorded by the microphone device, for example voice commands which are recordable by a further microphone device and serve for voice control of the medical-optical observation apparatus by the surgeon so that they can guide operating instruments, i.e., surgical instruments, with their hands. The term "substantially" takes account of the fact the extent of the acoustic directional area is frequency dependent and varies on the basis of the properties of the microphone device, depending on the frequency range of the recorded acoustic signals. Additionally, the extent varies depending on whether it is taken as a basis whether acoustic signals from outside of the directional area are in fact masked and hence not recorded, or whether they are recorded with very strong damping, and what limit defines very strong damping. In an exemplary embodiment, provision is made for an acoustic directional area which substantially corresponds to the optical field of view to not have an extent more than 10 percent larger than the optical field of view in any frequency range provided for the evaluation of the acoustic signals.

In an exemplary embodiment, the medical-optical observation apparatus is or includes a microscope device, typically a surgical microscope.

In one exemplary embodiment, the medical-optical observation apparatus includes means for keeping the spatial alignment of the acoustic directional area of the microphone device constant relative to the spatial alignment of the optical field of view when the spatial alignment of the optical field of view of the recording device is altered. By way of example, the medical-optical observation apparatus can be mounted in movable fashion, e.g., using a robotic stand, for the purposes of altering the spatial alignment of the optical field of view of the recording device. By way of example, means for keeping the relative alignment of the acoustic directional area constant relative to the optical field of view can be secure connections between the microphone device and the image recording device. If the microphone device includes a plurality of microphones, at least not all of which are securely connected to the image recording device, the means for keeping the relative alignment constant could also be, for example, a microphone control device, which is set up to dynamically adapt the acoustic directional area by way of a suitable actuation of the microphones in accordance with the changing alignment of the optical field of view.

In one exemplary embodiment, the medical-optical observation apparatus includes a microphone control device, which is set up to control a distance of the microphone device from the operating region on the basis of a focal value of the optical system of the image recording device. That is to say, the distance of the directional microphone is adapted in parallel with the change of the focal value of the optical system. Since, as a rule, the area of the operating region in which the next visual events are expected during the course of the operation are focused on, this is also the acoustic directional area in which noises relevant to the further course of the operation are to be expected.

In a further exemplary embodiment, the medical-optical observation apparatus includes a microphone control device, which is set up to adapt a width of the acoustic directional area of the microphone device on the basis of a change in a width of the optical signal range of the image recording device. Here, the width of the optical signal range is determined as the extent thereof vertical to the optical axis specified by the optical system. By way of example, this means that the width of an acoustic directional area in the form of a detection cone of a microphone device with a directional microphone is controlled to be parallel to the width of an optical field of view arranged around the optical axis of the image recording device in conical faction, and so the relative alignment with respect to one another remains constant and all noises, i.e., acoustic signals from noise sources, in the field of view can be captured at all times.

In one exemplary embodiment of the medical-optical observation apparatus, the microphone device includes a plurality of acoustic sensors, i.e., microphones. In this way, the acoustic capture volume, i.e., the acoustic directional area, can be better defined, for example by triangulation, and, for example, be adapted under microphone control device control, taking into account individual requirements, for example the shape of the operating region. Moreover, wherein the acoustic signals are recorded by a plurality of microphones, it is possible to better damp or eliminate, i.e., mask, background noises and hence disturbance noises. To this end, provision can also be made for post-processing with digital filtering by a data processing device.

In a further exemplary embodiment, a sensitivity of the microphone device in respect of acoustic signals at least also includes a frequency range outside of the human audible range. Instead of, or in addition to, acoustic signals audible to humans, the microphone device records, e.g., ultrasonic signals and/or infrasonic signals. If the microphone device only has one acoustic sensor, i.e., one microphone, the latter is designed to facilitate the recording of acoustic signals that are inaudible to humans in addition to, or instead of, recordings in the range of the human audible spectrum. If the microphone device includes a plurality of microphones, provision can alternatively also be made for the use of microphones that are designed specifically for certain different frequency ranges. Thus, in the case of surgical operations, it may be possible to record relevant acoustic signals, for example from the operating region, which lie below the human audible range. By way of example, this may be applicable to certain flow noises caused by the heartbeat of the patient. Acoustic signals in frequency ranges above the human audible range may be caused, for example, by operating instruments used during the course of the operation. The course of the operation may be able to be captured more completely by taking account of such acoustic signals.

In yet a further exemplary embodiment, the medical-optical observation apparatus includes a filter device for filtering the recorded acoustic signals, wherein the filter device is set up to at least partly compensate damping that is characteristic for a separation means arranged between the microphone apparatus and the operating region. This facilitates an "acoustic channel" through the separation means and the microphone device can be arranged in a non-sterile region that is separated from a sterile region that includes the operating region. By way of example, a drape cover or a drape is used as separation means. To this end, the filter device, which can be realized within the scope of a data processing device of the medical-optical observation apparatus when digital filtering is applied, is at least set up to compensate characteristic damping of the separation means. Additionally, provision can be made for the filtered signals to be amplified, for example.

In an exemplary embodiment, the medical-optical observation apparatus includes a data processing device, which is set up to detect noises relating to the operating region in the time profile of the recorded acoustic signals (by evaluating the stored electronic representations thereof). In particular, the evaluation includes the application of suitable digital filtering methods in order to extract information from the acoustic signals, for example the occurrence of new events and the occurrence or disappearance of noise sources. If the respective recording device does not yet carry out analog/digital conversion and, where necessary, associated pre-processing in order to generate digital representations, this can also be embodied as part of the data processing device, for the purpose of which the latter than has a suitable interface. For detecting individual phases of the course of the operation, it is possible, for example, to already evaluate the detected sequence and length of events and recognize different phases over the course of the operation.

In an exemplary embodiment, provision is made for the data processing device to moreover be set up to classify or identify the noises relating to the operating region on the basis of stored noises.

The stored noises, i.e., stored acoustic signals, can be stored as electronic representations. This includes direct storage of digital sampled values of the acoustic signals but can also be preprocessed data, wherein the preprocessing may include, for example, encoding or compression of the audio data and/or a parameterization of the signal profile, and/or parameter values that are based on descriptive models of the acoustic signals, for example generated with the aid of machine learning methods. The noises stored as electronic representations can also include different variants of the same.

By way of example, identifiable noises can be noises arising during cutting with scissors, noises of a suction device or a scalpel or noises when closing an aneurysm clip or when coagulating tissue, etc. Moreover, it is for example also possible to identify noises caused by the tissue, e.g., hemorrhaging, the tearing open of tissue, blood flow through vessels, etc. In this way, the identified noises and, for example, their sequence, volume, frequency or the change of the parameters over time can be used to make the detection of different phases over the course of the operation more precise and to possibly also recognize the phases and to recognize deviations from a known stored course of the operation phases and/or to predict subsequent operation phases. In this context, provision can also be made in one exemplary embodiment for comparisons to be also carried out with incorrectly performed stored sequences of operating procedures so that a warning can be issued, possibly in automated fashion, against continuing the operating procedure without change.

In a further exemplary embodiment, the data processing device is moreover set up to detect events relating to the operating region in the time profile of the recorded optical signals. Thus, using image and video analysis methods, it is possible, for example, to detect the start and/or the end of the use of certain aids and operating instruments, but also certain views of the treated tissue that are characteristic for the course of the operation, the stopping of bleeding, etc. In particular, provision is made in one exemplary embodiment for events to be detected in the optical signals and the acoustic signals and for these to be related to one another where applicable and for additional information to be obtained from the combination or for the reliability of the detections to thus be increased.

In one exemplary embodiment, the data processing device is moreover set up here to classify events relating to the operating region on the basis of stored views. In this way, it is possible, for example on the basis of stored views, to accurately determine utilized instruments or to compare the view of the operating region altered by the operation with the usual, intended views, for example an incision during the operation, the position or shape of a bone, or of tissue.

The stored views are stored as electronic representations. This includes direct storage of digital sampled values of image signals but could also be preprocessed data, wherein the pre-processing may include, for example, encoding or compression of the image data and/or a parameterization of the signal profile and/or parameter values, which are based on descriptive models of views of an entire operating region, but also of individual objects (e.g., a 3D model of an organ, bone or a surgical instrument to be used), wherein the models can be adapted on the basis of, for example, historical operating data, for example with the aid of machine learning methods. The views stored as electronic representations can also include different variants of the same.

In an exemplary embodiment, the data processing device is set up to ascertain features in the acoustic signals and optical signals recorded over the course of time and evaluate them in combination and to classify the course of time as associated progress phases on the basis of the evaluation.

Here, the combined evaluation can comprise both the combined simultaneous ascertainment of events on the basis of both the acoustic and the optical signals, and the ascertainment of events in the acoustic signals and events in the optical signals and the subsequent combined evaluation of the two event groups. To this end, the data processing unit is set up to carry out a sensor or information fusion algorithm, for example on the basis of a machine learning method, with which the respective associated phase of the course of the operation can be ascertained or predicted from the event information. In one exemplary embodiment, provision can be made for further data to also be taken into account in addition to data obtained from acoustic and optical signals, for example settings data of the medical-optical observation apparatus and the changes thereof, position data of a robotic arm, to which the medical-optical observation apparatus has been secured, acoustic signals, e.g., speech from the operating theater, recorded with a further microphone device, etc.

In one exemplary embodiment, the data processing device is moreover set up to assign the progress of phases to the phases of a surgical operation, i.e., to classify the progress phases determined on the basis of the undertaken signal evaluation in the time profile of the signals as phases corresponding to known or stored typical actual phases of a surgical operation.

In an exemplary embodiment, the data processing device is moreover set up to produce a surgery report, i.e., an operation report, on the basis of the assigned progress phases, i.e., the progress phases assigned to different phases of the surgical operation. A surgery report should at least describe the course of a performed operation, wherein, typically, further statements are also included, for example the goal of the operation and problems that arose and further statements from the patient file. In particular, in one exemplary embodiment provision can also be made for a comparison with progress sequences provided as a standard for the respective operation, for example present in a database, and for deviations of the associated progress phases from the envisaged phases to be determined. Determinable deviations can be, for example, the omission of a phase, the repetition of a phase, the deviation from an envisaged or mean duration of the phase, the deviation from an envisaged sequence of the phases or the performance of an unknown, non-envisaged phase or a phase actually provided for a different operation. By way of example, this offers the advantage that the attention of the surgeon when subsequently working through the surgery report can be steered directly to phases that may require explanation.

In a further exemplary embodiment of the medical-optical observation apparatus, settings of at least one operating modality of the medical-optical observation apparatus are assigned to the phases of the surgical operation and the data processing device is set up to alter current settings of the at least one operating modality of the medical-optical observation apparatus to the settings of the at least one operating modality which are assigned to a respective current phase of the surgical operation. By way of example, an operating modality of a medical-optical apparatus could be the zoom setting, the stand pose and the illumination, but also the selected representation on a screen, in which, e.g., additional operating menus or additional information items are superimposed or the image representation is altered or different representation modalities such as the fluorescence representation or OCT recordings are switched on (OCT—optical coherence tomography). Thus, for example, provision can be made for the zoom factor to be changed and for the alignment of the observation apparatus to be adapted by altering the stand pose and, optionally, also for the illumination of the operating region to be changed if it was identified that the operation has entered the next phase. By way of example, this can be implemented directly automatically or after approval by the surgeon or user of the medical-optical observation apparatus. To not to disturb the procedure much, provision can be made, for example, for the approval to be implemented by a voice command. The control of operating modalities on the basis of identified phases of the course of the operation is particularly expedient since the phases and phase changes are identified very reliably and precisely with the aid of the described combined evaluation of audio and image signals.

In an exemplary embodiment, the data processing device is set up to carry out a machine learning algorithm for ascertaining the features, e.g., events, and/or progress phases. Machine learning algorithms may be trainable and are based, for example, on the use of decision trees, support vector machines with a relevance feedback mechanism or other cluster methods.

In an exemplary embodiment, the machine learning algorithm includes at least one artificial neural network, for example a convolutional neural network. This offers the advantage that it can be "left" to the algorithm to itself determine characteristic and discriminative features from the analysis data in order to be able to correctly classify the respective associated phase of the course of the operation on the basis thereof. Here, the fusion of the image and acoustic data can be implemented at different points in the classification pipeline, i.e., for example, there can initially be separate classifications of the acoustic and optical signals and then a fusion of the ascertained data in order to ascertain the progress phases therefrom and in order to classify the latter or there can initially already be fusion of the acoustic and optical signals during the analysis, followed by a classification of the progress phases ascertained thus.

According to a second aspect of the disclosure, a computer program product includes code components which, when executed by a processor of a data processing device as a programmable device with processor and memory, set the data processing device up to be operated as data processing device of a medical-optical observation apparatus according to any one of the exemplary embodiments as per the first aspect of the disclosure. In this way, the advantages and peculiarities of the medical-optical observation apparatus according to the disclosure are also implemented within the scope of a computer program product. To this end, the computer program product is provided on a non-volatile computer-readable storage medium, for example, on which the computer program product is stored.

According to a third aspect of the disclosure, a non-volatile or non-transitory computer-readable storage medium is provided, stored on which are code components which, when executed by a processor of a data processing device, set the data processing device up to be operated as data processing device of a medical-optical observation apparatus according to any one of the exemplary embodiments as per the first aspect of the disclosure. This also implements the advantages and peculiarities of the medical-optical observation apparatus according to the disclosure within the scope of a computer-readable storage medium.

BRIEF DESCRIPTION OF THE DRAWINGS

The disclosure will now be described with reference to the drawing wherein:

FIG. 1 shows a schematic illustration of a medical-optical observation apparatus according to an exemplary embodiment of the disclosure.

DESCRIPTION OF EXEMPLARY EMBODIMENTS

It is understood that other exemplary embodiments can be used and structural or logical modifications can be undertaken, without departing from the scope of protection of the present disclosure. It is understood that the features of the various exemplary embodiments described can be combined with one another, provided there is no specific statement to the contrary. Therefore, the description should not be considered to be limiting and the scope of protection of the present disclosure is defined by the attached claims.

FIG. 1 shows a schematic illustration of a medical-optical observation apparatus 100 according to an exemplary embodiment of the disclosure. The medical-optical observation apparatus 100 can be a surgical microscope, in particular. The medical-optical observation apparatus 100 includes an image recording device 101 with an optical system 102. It has an optical field of view 103 (indicated by dashed lines). In the exemplary embodiment shown, the optical field of view 103 is embodied in conical fashion, in a manner concentric about the optical axis 104 (indicated as a dash-dotted line) of the optical system 102. Optical signals, i.e., image signals, of an operating region 105, i.e., a site, of a patient 106 are recorded with the image recording device 101. In FIG. 1, the patient 106 is shown lying on an operating table 107. Recording the optical signals includes capturing and steering the optical signals through the optical system 102 to an electronic image sensor 108 which generates an electronic representation of the optical signals that is stored continuously or at regular time intervals as a video, i.e., as a sequence of images over time. In the exemplary embodiment shown, the image recording device is provided to this end with an interface (not shown) and a wireless or wired connection to a storage device 109, in which the storage is implemented.

Moreover, the medical-optical observation apparatus 100 includes a microphone device 110 with an acoustic directional area 111 (indicated by full lines), for directional recording of acoustic signals with reference to the operating region 105. In the embodiment shown, the microphone device 110 includes a microphone or a plurality of microphones arranged around the optical system 102 of the image recording device 101 in ring-shaped fashion, the microphone or microphones being connected to the image recording device 101, wherein the acoustic directional area 111 likewise forms a conical region arranged in concentric fashion around the optical axis 104 directed at the operating region 105 and wherein the acoustic directional area 111 includes the optical field of view 103. In other exemplary embodiments, the optical field of view 103 can also include the acoustic directional area 111. To record, the microphone device 110 captures acoustic signals received from the acoustic directional area 111, carries out analog-digital conversion where necessary and stores electronic representations of the time profile of the acoustic signals. In the embodiment shown, the microphone device 110 is provided to this end with an interface (not shown) and a wireless or wired connection to the storage device 109, in which the storage is implemented, wherein acoustic and optical signals are stored with a common time reference.

Acoustic signals of noise sources outside of the acoustic directional area 111 are masked or suppressed by the microphone device 110. Acoustic signals are recorded directly from the operating region 105 but also, for example, from surgical instruments which are used in the optical field of view 103 in or on the operating region 105. By way of example, in FIG. 1 a surgeon 112 uses a surgical operating instrument 113 on the operating region 105 of the patient 106, from where both operating noises and noises generated thereby in the operating region 105, e.g., when cutting tissue or when liquid emerges, etc., are recorded. Thus, it is possible to record many acoustic signals, some of which are also very quiet, during the course of the operation, said signals containing information about the progress of the operation which facilitate an identification or assignment of a process to a specific phase over the course of the surgical operation.

In the exemplary embodiment shown, the microphone device 110 is securely connected to the image recording device 101, and so the spatial alignment of the acoustic directional area 111 of the microphone device 110 remains constant relative to the spatial alignment of the optical field of view 103 when the spatial alignment of the optical field of view 103 of the image recording device 101 is altered, even if, like in the embodiment for changing the spatial alignment of the optical field of view 103 shown in FIG. 1, the image recording device 101 is attached to a movable robotic stand 114.

In one exemplary embodiment, the microphone device 110 is securely connected to the image recording device 101 but attached in a manner linearly displaceable parallel to the optical axis by way of a rail system (not shown), for example. A microphone control device, which can be realized either separately or as part of a data processing device 115, then is provided to alter a distance of the microphone device 110 from the operating region 105 on the basis of a focal value of the optical system 102 of the image recording device 101 such that the distance of the microphone device 110 is adapted on the basis of the change of the focal value of the optical system 102. The microphone control device can also be set up to adapt a width of the acoustic directional area 111 of the microphone device 110 on the basis of a change in the width of the optical field of view 103 of the image recording device 101.

In the exemplary embodiment shown, the data processing device 115 is a programmable device which includes a processor 116 and a memory 117, for example a random access memory, into which code components of a computer program product are loaded which, when executed by the processor 116, set the data processing device 115 up to control the medical-optical observation apparatus 100 and to evaluate the recorded signals, in particular to detect noises relating to the operating region 105 in the time profile of the recorded acoustic signals (by evaluating the stored electronic representations thereof), and to extract information in order to recognize individual phases over the course of the operation. In the process, the data processing device 115 is moreover programmed to classify or identify the noises on the basis of stored noises.

Moreover, the data processing device 115 is configured to detect events in or on the operating region 105, for example the start and/or the end of the use of the surgical operating instrument 113, in the time profile of the recorded optical signals, i.e., in the sequence of recorded images.

The data processing device 115 relates the events detecting the optical and the acoustic signals to one another and thus increases the reliability of the detections. Features are ascertained in the acoustic signals and optical signals recorded over the course of time, which features allow the course of time to be divided into associated progress phases. To this end, the data processing device 115 carries out an information fusion algorithm as a machine learning algorithm, which is based on a convolutional neural network, for example. To train the latter, the phase division ascertained by the data processing unit 115 is displayed at least visually to the surgeon 112 after the operation as a chapter of operation documentation, i.e., a surgery report, for example in an image output device 118, i.e., a screen, of the medical-optical observation apparatus 100, with which the surgeon 112 is provided with the optical signal recorded by the image recording device 101 during the operation, wherein a different image output device may also be provided in other embodiments. For training purposes, the surgeon can then confirm, reject or correct the ascertained phase division.

The FIGURE is not true in details and true to scale. For this reason, functional details disclosed here should not be understood to be limiting, but merely to be an illustrative basis that gives guidance to a person skilled in this technical field for using the present disclosure in various ways. It is also understood that boundaries between units of the presented observation apparatus serve to illustrate the functionality of the apparatus and that, in other exemplary embodiments, units can be, e.g., combined or functionalities can be assigned to other units. Thus, for example, in other exemplary embodiments, the image recording device 101 shown in FIG. 1 can itself contain the storage device 109 or realize a microphone control device as a separate unit, in order to name a few examples. In other words: The present descriptions are offered for the purpose of illustrating specific embodiments and should not be interpreted as being a limitation of the subject matter disclosed.

The expression "and/or" used here, when it is used in a series of two or more elements, means that any of the elements listed can be used alone, or any combination of two or more of the elements listed can be used. For example, if a structure is described as containing the components A, B and/or C, the structure can contain A alone; B alone; C alone; A and B in combination; A and C in combination; B and C in combination; or A, B, and C in combination.

The present disclosure has been described in detail on the basis of exemplary embodiments for purposes of explanation. A person skilled in the art recognizes that details that were described with reference to one embodiment can also be used in other embodiments. Therefore, the disclosure is not intended to be restricted to individual embodiments, but rather only by the appended claims.

Exemplary embodiments of the disclosure are also the following:

Exemplary embodiment 1: A medical-optical observation apparatus, comprising an image recording device with an optical system and an optical field of view, for recording optical signals from an operating region; and a microphone device with an acoustic directional area, for the directed recording of acoustic signals with reference to the operating region, wherein the acoustic directional area includes the optical field of view, wherein a storage device for storing the optical signals is assigned to the image recording device and a storage device for storing the acoustic signals is assigned to the microphone device, the optical and acoustic signals being able to be stored with a common time reference such that it is possible to temporally relate the signals to one another during an evaluation.

Exemplary embodiment 2: The medical-optical observation apparatus of exemplary embodiment 1, wherein the microphone device is set up to record acoustic signals from noise sources in the optical field of view of the image recording device and dampen other acoustic signals.

Exemplary embodiment 3: The medical-optical observation apparatus of exemplary embodiment 1 or exemplary embodiment 2, wherein the acoustic directional area substantially corresponds to the optical field of view.

Exemplary embodiment 4: The medical-optical observation apparatus of any one of the preceding exemplary embodiments, wherein the medical-optical observation device includes a microscope device, typically a surgical microscope.

Exemplary embodiment 5: The medical-optical observation apparatus of any one of the preceding exemplary embodiments, moreover comprising: means for keeping the spatial alignment of the acoustic directional area of the microphone device constant relative to the spatial alignment of the optical field of view when the spatial alignment of the optical field of view of the image recording device is altered.

Exemplary embodiment 6: The medical-optical observation apparatus of any one of the preceding exemplary embodiments, comprising: a microphone control device, set up to control a distance of the microphone device from the operating region on the basis of a focal value of the optical system of the image recording device.

Exemplary embodiment 7: The medical-optical observation apparatus of any one of exemplary embodiments 1 to 5, comprising a microphone control device, set up to adapt a width of the acoustic directional area of the microphone device on the basis of a change in a width of the optical field of view of the image recording device.

Exemplary embodiment 8: The medical-optical observation apparatus of any one of the preceding exemplary embodiments, wherein the microphone device includes a plurality of acoustic sensors.

Exemplary embodiment 9: The medical-optical observation apparatus of any one of the preceding exemplary embodiments, wherein a sensitivity of the microphone device in respect of acoustic signals at least also includes a frequency range outside of the human audible range.

Exemplary embodiment 10: The medical-optical observation apparatus of any one of the preceding exemplary embodiments, comprising a filter device for filtering the recorded acoustic signals, wherein the filter device is set up to at least partly compensate damping that is characteristic for a separation means arranged between the microphone device and the operating region.

Exemplary embodiment 11: The medical-optical observation apparatus of any one of the preceding exemplary embodiments, comprising: a data processing device, set up to detect noises relating to the operating region in the time profile of the recorded acoustic signals.

Exemplary embodiment 12: The medical-optical observation apparatus of exemplary embodiment 11, wherein the data processing device is moreover set up to classify noises relating to the operating region on the basis of stored noises.

Exemplary embodiment 13: The medical-optical observation apparatus of exemplary embodiment 11 or exemplary embodiment 12, wherein the data processing device is moreover set up to detect events relating to the operating region in the time profile of the recorded optical signals.

Exemplary embodiment 14: The medical-optical observation apparatus of exemplary embodiment 13, wherein the data processing device is moreover set up to classify events relating to the operating region on the basis of stored views.

Exemplary embodiment 15: The medical-optical observation apparatus of any one of exemplary embodiments 11 to 14, wherein the data processing device is set up to ascertain features in the acoustic signals and optical signals recorded over the course of time and evaluate them in combination and to classify the course of time as associated progress phases on the basis of the evaluation.

Exemplary embodiment 16: The medical-optical observation apparatus of exemplary embodiment 15, wherein the data processing device is moreover set up to assign progress phases to phases of a surgical operation.

Exemplary embodiment 17: The medical-optical observation apparatus of exemplary embodiment 16, wherein the data processing device is set up to generate a surgery report on the basis of the assigned progress phases.

Exemplary embodiment 18: The medical-optical observation apparatus of exemplary embodiment 16 or exemplary embodiment 17, wherein settings of at least one operating modality of the medical-optical observation apparatus are assigned to the phases of the surgical operation and the data processing device is set up to alter current settings of the at least one operating modality of the medical-optical observation apparatus to the settings of the at least one operating modality which are assigned to a respective current phase of the surgical operation.

Exemplary embodiment 19: The medical-optical observation apparatus of any one of exemplary embodiments 15 to 18, wherein the data processing device is set up to carry out a machine learning algorithm for ascertaining the features and/or progress phases.

Exemplary embodiment 20: The medical-optical observation apparatus of exemplary embodiment 19, wherein the machine learning algorithm includes an artificial neural network.

Exemplary embodiment 21: A computer program product having code components which, when executed by a processor of a data processing device, set the data processing device up to be operated as data processing device of a medical-optical observation apparatus of any one of exemplary embodiments 11 to 20.

Exemplary embodiment 22: A non-volatile computer-readable storage medium, stored in which are code components which, when executed by a processor of a data processing device, set the data processing device up to be operated as data processing device of a medical-optical observation apparatus of any one of exemplary embodiments 11 to 20.

LIST OF REFERENCE NUMERALS

100 Medical-optical observation apparatus
101 Image recording device
102 Optical system
103 Optical field of view
104 Optical axis
105 Operating region
106 Patient
107 Operating table
108 Electronic image sensor
109 Storage device
110 Microphone device
111 Acoustic directional area
112 Surgeon
113 Surgical operating instrument
114 Robotic stand
115 Data processing device
116 Processor
117 Memory
118 Image output device

What is claimed is:

1. A medical-optical observation apparatus comprising:
an image recording device with an optical system and an optical field of view configured to capture light rays and to record optical signals from an operating region; and
a microphone device with an acoustic directional area configured to directedly record acoustic signals with reference to the operating region,
wherein the acoustic directional area includes the optical field of view,
wherein a first storage device for storing the optical signals is assigned to the image recording device and a second storage device for storing the acoustic signals is assigned to the microphone device, and
wherein the optical signals and the acoustic signals can be stored with a common time reference such that it is possible to temporally relate the optical signals and the acoustic signals to one another during an evaluation.

2. The medical-optical observation apparatus as claimed in claim 1, wherein the microphone device is configured to record the acoustic signals from noise sources in the optical field of view of the image recording device and to dampen other acoustic signals.

3. The medical-optical observation apparatus is claimed in claim 1, wherein the acoustic directional area substantially corresponds to the optical field of view.

4. The medical-optical observation apparatus as claimed in claim 1, further comprising a microscope device or a surgical microscope.

5. The medical-optical observation apparatus as claimed in claim 1, further comprising means for keeping a spatial alignment of the acoustic directional area of the microphone device constant relative to the spatial alignment of the optical field of view when the spatial alignment of the optical field of view of the image recording device is altered.

6. The medical-optical observation apparatus as claimed in claim 1, further comprising a microphone control device configured to control a distance of the microphone device from the operating region based on a focal value of the optical system of the image recording device.

7. The medical-optical observation apparatus as claimed in claim 1, further comprising a microphone control device configured to adapt a width of the acoustic directional area of the microphone device based on a change in the width of the optical field of view of the image recording device.

8. The medical-optical observation apparatus as claimed in claim 1, wherein a sensitivity of the microphone device in respect of the acoustic signals at least also comprises a frequency range outside of a human audible range.

9. The medical-optical observation apparatus as claimed in claim 1, further comprising a filter device configured to filter the recorded acoustic signals, and wherein the filter device is configured to at least partly compensate damping that is characteristic for a separation means arranged between the microphone device and the operating region.

10. The medical-optical observation apparatus as claimed in claim 1, further comprising a data processing device configured to detect noises relating to the operating region in a time profile of the recorded acoustic signals.

11. The medical-optical observation apparatus as claimed in claim 10, wherein the data processing device is further configured to classify noises relating to the operating region based on stored noises.

12. The medical-optical observation apparatus as claimed in claim 10, wherein the data processing device is further configured to detect events relating to the operating region in the time profile of the recorded optical signals.

13. The medical-optical observation apparatus as claimed in claim 12, wherein the data processing device is further configured to classify events relating to the operating region based on stored views.

14. The medical-optical observation apparatus as claimed in claim 10, wherein the data processing device is configured to determine features in the acoustic signals and the optical signals recorded over a course of time and evaluate them in combination and to classify the course of time as associated progress phases based on the evaluation.

15. The medical-optical observation apparatus as claimed in claim 14, wherein the data processing device is further configured to assign progress phases to phases of a surgical operation.

16. The medical-optical observation apparatus as claimed in claim 15, wherein the data processing device is configured to generate a surgery report based on the assigned progress phases.

17. The medical-optical observation apparatus as claimed in claim 15, wherein settings of at least one operating modality of the medical-optical observation apparatus are assigned to the phases of the surgical operation and the data processing device is configured to alter current settings of at least one operating modality of the medical-optical observation apparatus to the settings of the at least one operating modality which are assigned to a respective current phase of the surgical operation.

18. The medical-optical observation apparatus as claimed in claim 14, wherein the data processing device is configured to carry out a machine learning algorithm to determine the features and/or the progress phases.

19. A computer program product having code components which, when executed by a processor of the data processing device, configure the data processing device to be operated as the data processing device of the medical-optical observation apparatus as claimed in claim 10.

20. A non-volatile computer-readable storage medium encoded with instruction which, when executed by a processor of the data processing device, cause the data processing device to operate as the data processing device of the medical-optical observation apparatus as claimed in claim 10.

* * * * *